United States Patent
Blum et al.

[11] Patent Number: 5,891,919
[45] Date of Patent: Apr. 6, 1999

[54] DENATONIUM CAPSAICINATE AND METHODS OF PRODUCING THE SAME

[75] Inventors: Melvin Blum, Wantagh, N.Y.; Michael Roitberg, Highland Park, N.J.

[73] Assignee: Burlington Bio-Medical & Scientific Corp., Farmingdale, N.Y.

[21] Appl. No.: 929,621

[22] Filed: Sep. 19, 1997

[51] Int. Cl.$^6$ .......................... A01N 31/16; C07C 233/05
[52] U.S. Cl. .................. 514/625; 106/14.05; 106/15.05; 106/172.1; 106/190.1; 252/301.16; 252/392; 252/401; 424/78.09; 424/405; 424/406; 424/408; 424/439; 424/442; 504/345; 514/643; 554/52; 564/158
[58] Field of Search ...................................... 564/158, 282, 564/285; 106/14.05, 15.05, 172.1, 190.1; 252/301.16, 392, 401; 424/78.09, 405, 406, 408, 439, 642; 514/643, 556, 557, 558, 563, 625; 504/345; 554/52

[56] References Cited

U.S. PATENT DOCUMENTS

| | | |
|---|---|---|
| 3,080,327 | 3/1963 | Hay . |
| 3,268,577 | 8/1966 | Hay . |
| 4,005,038 | 1/1977 | Minkoff . |
| 4,438,046 | 3/1984 | Grew et al. . |
| 4,652,577 | 3/1987 | Hollander et al. . |
| 4,661,504 | 4/1987 | Hollander et al. . |
| 5,094,782 | 3/1992 | Chen et al. . |
| 5,322,862 | 6/1994 | Kurata et al. . |
| 5,397,385 | 3/1995 | Watts . |
| 5,403,868 | 4/1995 | Reid et al. . |
| 5,456,916 | 10/1995 | Kurata et al. . |

OTHER PUBLICATIONS

Dahl et al, Brain Research, 756, pp. 22–34, 1997.
Nelson, E.K. e al., "Constitution of Capsaicin. III," vol. XLV *Journal of American Chemistry*, 2179–1881 (1923).

*Primary Examiner*—Shailendra Kumar
*Attorney, Agent, or Firm*—Oliff & Berridge, PLC

[57] ABSTRACT

A new compound, Denatonium Capsaicinate, and a method of producing the same are disclosed. Denatonium Capsaicinate provides an enhanced bitter and/or spicy, pungent flavor and may be used as an aversive agent, biocide, antifoulant and flavorant, for example. It is formed by reaction of a denatonium compound, Lidocaine or Lidocaine derivative with Capsaicin or a derivative thereof.

20 Claims, No Drawings

DENATONIUM CAPSAICINATE AND METHODS OF PRODUCING THE SAME

BACKGROUND OF THE INVENTION

1. Field of Invention

This invention relates to a compound, methods of producing the compound, and means of using the compound as an aversive agent. In particular, this invention relates to the novel compound Denatonium Capsaicinate.

2. Description of Related Art

The use of denatonium compounds, in particular Denatonium Benzoate and Denatonium Saccharide, as aversive agents is known. See U.S. Pat. Nos. 3,080,327, 3,268,577, 4,661,504 and 4,652,577. Denatonium is derived from Lidocaine (N,N-diethylamino-2,6-dimethylacetanilide) The structure in common between Lidocaine and denatonium compounds is shown in Formula 1:

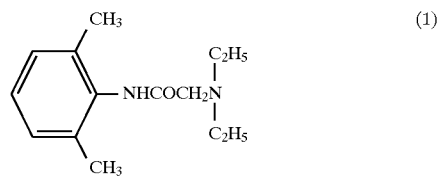

Denatonium compounds are frequently incorporated into compositions or coatings in order to deter either ingestion by humans or to repel animals, reptiles, fish and birds from an article coated therewith. See U.S. Pat. No. 4,005,038. Denatonium compounds are also used as denaturants for alcohol and tallow (U.S. Pat. No. 4,438,046), and as bitter flavoring agents in food. Generally, the taste threshold level for denatonium compounds is from about 1 part in 10 million to 1 part in 100 million, and the aftertaste can last from several seconds to several minutes. However, the taste of these compounds is not always perceived by certain animals, such as certain species of rodents, dogs, deer, etc. Therefore, these compounds are not always effective as an aversive agent for all animals.

A second aversive agent known in the art is Capsaicin and its derivatives. See E. K. Nelson and L. E. Dawson, "Constitution of Capsaicin. III," Vol. XLV *J. Am. Chem.*, 2179–2181 (1923). The structures of both natural and synthetic Capsaicin are shown below in Formulas 2a and 2b, respectively.

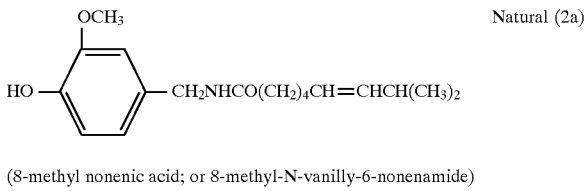

(8-methyl nonenic acid; or 8-methyl-N-vanilly-6-nonenamide)

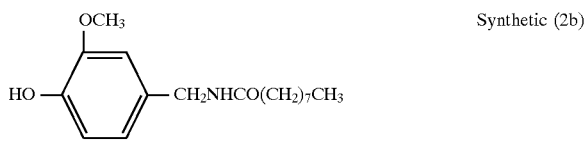

(N-4-hydroxy-3-methoxybenzyl)-8-methyl non-6-enamide; or nonanoyl vanillylamide)

Capsaicin provides a hot, spicy, pungent flavor as well as a numbing, burning or tingling effect when applied orally or topically. Capsaicin is known to be a powerful irritant that can cause selective degeneration of sensory neurons that mediate chemogenic or trigeminal pain. Capsaicin and its derivatives are principally used as an irritant; a flavorant from about 1 part in 100,000 parts; an animal repellent (U.S. Pat. Nos. 5,322,862 and 5,456,916); an antifoulant (U.S. Pat. No. 5,397,385); a carminative; in neural biological research (U.S. Pat. No. 5,094,782); and in pharmaceuticals (U.S. Pat. No. 5,403,868). Both the natural and synthetic compounds of Capsaicin have been found to be very effective for these uses.

Although both denatonium compounds and capsaicin compounds provide an offensive flavor and are therefore useful as aversive agents, a new and useful compound exhibiting an enhanced bitter and/or sharp taste is most desirable. Accordingly, it is an object of the present invention to provide a new compound, Denatonium Capsaicinate, that is effective in very low concentrations to provoke a bitter and/or spicy, pungent flavor and/or to produce a chemogenic effect.

It is a further object of the invention to provide a new compound, Denatonium Capsaicinate, that is effective as a biocide.

It is a further object of the invention to provide a new compound, Denatonium Capsaicinate, that is effective as an antifoulant.

SUMMARY OF THE INVENTION

In accordance with the objects of this invention, there is provided herein the compound Denatonium Capsaicinate, which is more bitter than other known denatonium or capsaicin compounds. The compound and its derivatives provide an extremely bitter and/or spicy, pungent flavor that lasts considerably longer and has greater intensity than either denatonium compounds, capsaicin compounds, or mixtures thereof. The compound further provides biocidal and antifoulant properties.

DETAILED DESCRIPTION OF PREFERRED EMBODIMENTS

The chemical name of Denatonium Capsaicinate is denatonium nonyl vanylamide. When made with synthetic Capsaicin, Denatonium Capsaicinate has an empirical formula of $C_{38}H_{55}N_3O_4$, a weight-average molecular weight of 617.83, and a structure as represented below by Formula 3:

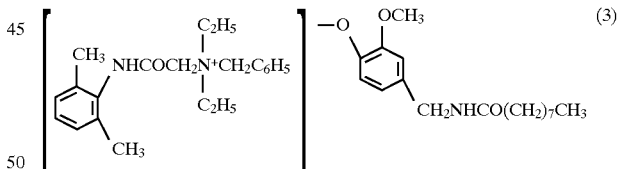

When made with natural Capsaicin, Denatonium Capsaicinate may have an empirical formula of $C_{38}H_{56}N_3O_5$ and a weight average molecular weight of 634.83. The structure of Denatonium Capsaicinate made with natural Capsaicin may vary due to the presence of naturally occurring homologs of Capsaicin. Therefore, a mixture of various structures may occur. However, the structure of Denatonium Capsaicinate made with natural Capsaicin is primarily represented by Formula 3. Therefore, Denatonium Capsaicinate made with either natural or synthetic Capsaicin has substantially the same properties. The name "Denatonium Capsaicinate" hereinafter refers to both compounds, unless otherwise stated.

Denatonium Capsaicinate is a white crystalline or powdered substance having a melting point of about 65° C. The bitter taste and stinging or burning sensation provided by the compound can last for as long as ten minutes, and in some cases, up to half an hour. The taste threshold is about 1 part in ten million parts, making Denatonium Capsaicinate a powerful aversant. Denatonium Capsaicinate is also known to have both biocidal and antifoulant properties.

Denatonium Capsaicinate is practically insoluble in water and paraffin, but is soluble in alcohols, ethylene and propylene glycol, methylcellusolve, n-methylpyrrolidone, dimethylsulfoxide (DMSO), ethers, chloroform, benzene and the like. Unlike other denatonium compounds, a fine powder of Denatonium Capsaicinate forms a colloidal suspension in certain solutions. Therefore, it is more easily dispersed into polymers, plasticizers and solutions. This is useful for incorporating Denatonium Capsaicinate into coatings for materials, or the material composition itself.

According to the present invention, Denatonium Capsaicinate can be synthesized by first producing Denatonium Hydroxide from a Lidocaine base. The Denatonium Hydroxide is reacted with synthetic or natural Capsaicin, or a derivative thereof, in an appropriate solvent. The subsequent product, Denatonium Capsaicinate, is purified by vacuum, air or spray drying at about 15°–50° C. The use of natural Capsaicin results in a less pure final product than the synthetic form due to various homologs usually present in the natural form.

Alternatively, the combination of any denatonium compound, Lidocaine, or a Lidocaine derivative in an aqueous, glycol, polyol, dimethylsulfoxide (DMSO), alcohol solution or combination thereof with Capsaicin or any of its derivatives will form some Denatonium Capsaicinate. Generally, the yield of Denatonium Capsaicinate formed in this manner will be low, from about 0.01 to about 0.50% by weight of the resultant composition. However, the yield may be more or less depending upon the amount and type of reactants, solution and reaction conditions. Surfactants such as Tweens™, Spans™, sarcosinates, sulfosuccinates, nonoxynols, and polyethylene glycols (PEG's), for example, may be added to the solution to accelerate the formation of Denatonium Capsaicinate.

The present invention is also directed to derivatives of Denatonium Capsaicinate, as shown below by Formula 4:

$$\left[ \underset{R_1}{\underset{|}{\bigodot}} \text{—NHCR}_2\text{CH}_2\overset{R_3}{\underset{R_4}{\underset{|}{N^+}}}\text{CH}_2\text{R}_5 \right] \quad \underset{\text{CH}_2\text{NHCR}_7\text{R}_8}{\overset{-\text{O}}{\underset{|}{\bigodot}}\text{R}_6} \quad (4)$$

wherein R and $R_1$ are independently selected from the group consisting of H and $C_{1-4}$ alkyl; $R_2$ and $R_7$ are independently selected from S or O; $R_3$, $R_4$ and $R_5$ are independently selected from a phenyl or substituted phenyl group; $R_6$ is H or $OR_9$, wherein $R_9$ is H or $C_{1-4}$ alkyl; and $R_8$ is $C_{7-12}$ alkyl, $C_{7-12}$ alkenyl, or $C_{7-12}$ alkynyl.

In embodiments, Denatonium Capsaicinate, its derivatives and salts, hereafter referred to as "Denatonium Capsaicinate," may be added to paints, lacquers, varnishes, glues, adhesives, gums, rubbers, polymers, coating compositions, and the like. The resultant compositions may be used to coat a layer or film on a fiber optic cable, an electric cable, a pipe, a hose, a wall, a boat hull, or other material.

Because a fine powder of Denatonium Capsaicinate forms a colloidal suspension, it can easily be added to plasticizers, silicones, epoxies, oils, waxes, and the like, and impregnated into various polymers such as polyethylenes, polypropylenes, styrenes, polyesters, polyurethanes, polyolefins, acrylics, phenolics, polyvinyl chlorides (PVCs), Teflons, nylons, rubbers, silicones and the like, to form fibers, a sheath or film layer for wrapping around a cable, wire, hose, or the like. The Denatonium Capsaicinate is added to the polymer in an amount of from about 0.01–10.0% by weight of the total composition. The Denatonium Capsaicinate may be added directly to the polymer in a liquid state, or formed into a colloidal suspension with a plasticizer or the like and then added to the polymer.

In embodiments, Denatonium Capsaicinate may be added to coatings or polymers for forming a sheath, for example, for application to electrical wires, hoses, pipes and the like to prevent animal attack. Similarly, a coating comprising Denatonium Capsaicinate, such as paint, varnish, lacquer, stain, sealant and the like, may be applied to other materials, such as outdoor furniture, sheds, or even houses, to deter animals, in particular, squirrels, from gnawing on and destroying them. Denatonium Capsaicinate further acts as a potent aversive agent when applied to seeds or like foodstuffs to prevent ingestion by birds and foraging animals.

Denatonium Capsaicinate may also be used in a coating applied to boat hulls, underwater structures, and the like as an antifoulant. Alternatively, Denatonium Capsaicinate may be incorporated into the materials for forming such structures. This will prevent marine life, in particular, barnacles and algae, from growing on the structures. Denatonium Capsaicinate is particularly suited for this use because it is insoluble in water and has both antifoulant and biocidal properties.

Denatonium Capsaicinate may also be used as a biocide to prevent or stop fungi, mildew and other microorganisms from growing. The affected area may be sprayed or coated with a solution containing Denatonium Capsaicinate; treated with a sticky or paste-like compound containing Denatonium Capsaicinate by spraying, spreading, smearing or the like; or sprinkled with a powder containing Denatonium Capsaicinate.

In other embodiments, Denatonium Capsaicinate may be added to medical dressings such as sutures and bandages, as well as to salves, creams, lotions, ointments and other like medical treatments in order to prevent animals from removing these materials by biting, gnawing, chewing or licking after veterinarial procedures. Further, because of its relationship to Capsaicin, derivatives thereof, and Lidocaine and its derivatives, Denatonium Capsaicinate, its derivatives and salts, may have medical uses such as in pharmacological compositions.

In further embodiments, Denatonium Capsaicinate may be used as an insect repellent. Denatonium Capsaicinate may also be combined with saponins, such as soy, yucca, quillaia and the like, and surfactants, such as sodium, potassium or ammonium lauryl sulfates and the like, to form an effective snake, shark or fish repellent. In embodiments, the repellent composition may comprise surfactant in an amount of from about 30–70% by weight of the total composition, saponin in an amount of from about 25–65% by weight of the total composition, and from about 0.01–15% by weight Denatonium Capsaicinate. Other effective compositions will be obvious to one of ordinary skill in the art. Further, Denatonium Capsaicinate may be formed into an aerosol or placed in a pressure sprayer to form a personal protectant to ward off human or animal attackers.

In other embodiments, Denatonium Capsaicinate may be added to such products as cigarettes or nail lacquer in order to deter habits such as smoking or nail biting. It may also be formed into an effective coating for deterring thumb or finger sucking by young children. It also may be added to dangerous household chemicals as an aversant. Further, Denatonium Capsaicinate, like other denatonium compounds, may be used as a denaturant.

Furthermore, Denatonium Capsaicinate may be used as a food additive, similar to Oleoresin Capsicum, Capsaicin and Capsaicin derivatives.

Other possible uses of Denatonium Capsaicinate as an aversive agent, biocide, antifoulant, flavorant, or denaturant, for example, will be obvious to those of ordinary skill in the art.

A method of forming Denatonium Capsaicinate is described in the Examples below. Other methods of formation are possible. In particular, Lidocaine, its derivatives, or any denatonium compound may be used as the starting point for the production of Denatonium Capsaicinate. However, the greatest yield and highest purity appear to be achieved by using Denatonium Hydroxide and synthetic Capsaicin.

Examples of formulations are also given. These examples are not meant to limit the disclosure. Other methods of formation and formulations may be used as would be known to one of ordinary skill in the art.

All references cited herein are incorporated by reference.

EXAMPLES

Example 1

Method of forming Denatonium Capsaicinate

About 500 ml of pure isopropanol is added to a three necked glass flask equipped with a stirrer (60–80 rpm), thermometer, reflux (straight-run) and condenser. About 9.4 g of KOH (based on 100 percent content) is added to the isopropanol with stirring. The reaction mass is heated to its boiling point and held until total dissolution of the KOH occurs. The solution is then cooled to about 50°–5520 C. About 60 g of Denatonium Chloride is added to the cooled solution. The mixture is stirred for thirty to forty minutes at about 50°–55° C. The resulting solution is cooled to about 18°–2020 C. and transferred to a filter with filtering paper, wherein potassium chloride precipitate is separated. The mother liquor is recycled to the same flask and about 54 g of Capsaicin is added. The reaction mixture is heated to its boiling point and refluxed for about 1–1.5 hours. The reflux condenser is then replaced with a straight run condenser and the isopropanol-water azeotrope is distilled off. The reaction mass is boiled off to about 200 ml in volume, cooled to an ambient temperature, and transferred to a polyethylene or similar vessel and refrigerated at about 3°–5° C. for about ten to twelve hours. The precipitated crystals are filtered, washed on a filter with cyclohexane or petroleum ether, and air or vacuum dried at ambient temperature.

The reaction process, starting with Denatonium Chloride and adding synthetic Capsaicin, is shown below in Formulas 5a and 5b.

REACTION PROCESS

Step 1.

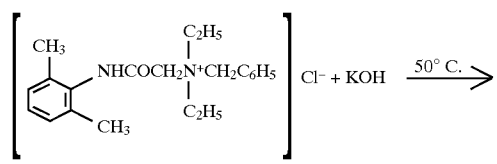
(5a)

Step 2.

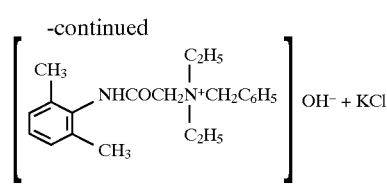

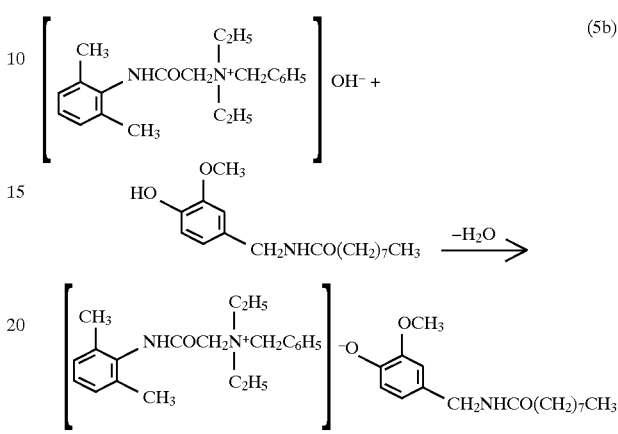

Example 2

| Denatonium Capsaicinate | 5% |
| --- | --- |
| Saponin | 45% |
| Sodium Lauryl Sulfate | 50% |

The above ingredients are mixed thoroughly. The composition can be used as a shark, snake, reptile or fish repellent.

Example 3

| Denatonium Capsaicinate | 20% |
| --- | --- |
| Propylene glycol | 80% |

A combination solution and colloidal suspension of Denatonium Capsaicinate in propylene glycol is formed. The combination solution/colloidal suspension or slurry may be added to plasticizers, polymers, oils or other like substances during further processing into paints, varnishes, lacquers, or other coating materials.

Example 4

| Denatonium Capsaicinate | 0.5% |
| --- | --- |
| Dimethyl Ether | 79.0% |
| Alcohol | 20.5% |

A solution of Denatonium Capsaicinate in a mixture of dimethyl ether and alcohol is formed. The dimethyl ether acts as a propellant. The mixture may be used in a pressurized spray to ward off human or animal attack.

Example 5

Crystalline or powdered Denatonium Capsaicinate are added to fillers, such as starches and inert type sugars, in an amount of from about 0.05–10%. The resultant dry powder, or sticky composition (if a wax or the like is added), is used to deter insects and rodents, particularly in residences.

We claim:
1. A compound, Denatonium Capsaicinate.
2. The compound of claim 1 in crystalline form.
3. Derivatives of the compound of claim 1 having the formula:

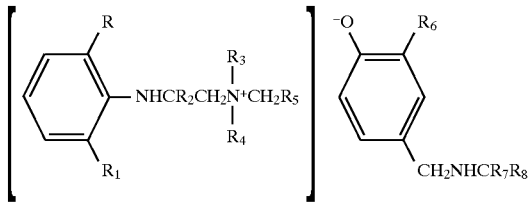

wherein R and $R_1$ are independently selected from the group consisting of H and $C_{1-4}$ alkyl; $R_2$ and $R_7$ are independently selected from S or O; $R_3$, $R_4$ and $R_5$ are independently selected from a phenyl or substituted phenyl group; $R_6$ is H or $OR_9$, wherein $R_9$ is H or $C_{1-4}$ alkyl; and $R_8$ is $C_{7-12}$ alkyl, $C_{7-12}$ alkenyl, or $C_{7-12}$ alkynyl.

4. A composition comprising the compound of claim 1, a derivative of the compound of claim 1, or a combination thereof.

5. The composition of claim 4, wherein said composition is a liquid.

6. The composition of claim 5, wherein said liquid is coated or sprayed on a material.

7. The composition of claim 6, wherein the material is selected from the group consisting of an agricultural product, a food product, a smoking product, a medical dressing, a boat, an underwater structure, a sheath, a wire, a hose and a pipe.

8. The composition of claim 4, wherein said composition is a food additive.

9. A method of deterring animal attack comprising treating a material with the composition of claim 4.

10. The method of claim 9, wherein treating said material comprises incorporating the composition into the material.

11. The method of claim 9, wherein the method of treating the material comprises coating the composition onto the material.

12. A method of deterring an animal attack comprising spraying the composition of claim 4 at said animal.

13. The method of claim 12, wherein the animal is selected from the group consisting of a mammal, a fish, a bird, and a reptile, wherein the mammal includes a human.

14. A method of preventing microorganism growth, comprising applying onto or incorporating into a material a biocidal composition comprising the compound of claim 1, a derivative of the compound of claim 1, or a combination thereof.

15. A method of providing antifoulant protection, comprising applying onto or incorporating into a material the composition of claim 4.

16. A method of preparing Denatonium Capsaicinate comprising:
    forming a compound; and
    reacting said compound with Capsaicin, a capsaicin derivative, or a combination thereof,
wherein said compound is Lidocaine, a Lidocaine derivative or a denatonium compound.

17. The method of claim 16, wherein the denatonium compound is selected from the group consisting of Denatonium Benzoate, Denatonium Chloride, Denatonium Saccharide and Denatonium Hydroxide.

18. The method of claim 16, wherein forming said compound comprises forming Denatonium Hydroxide from one or more of Lidocaine, a Lidocaine derivative, Denatonium Benzoate, Denatonium Chloride, or Denatonium Saccharide.

19. A method of preparing Denatonium Capsaicinate comprising:
    forming Denatonium Hydroxide; and
    reacting Denatonium Hydroxide with Capsaicin, a capsaicin derivative, or a combination thereof.

20. The method of claim 19, wherein a starting material for forming Denatonium Hydroxide is selected from the group consisting of Lidocaine, a Lidocaine derivative, Denatonium Chloride, Denatonium Benzoate, and Denatonium Saccharide.

* * * * *